United States Patent [19]
Asnis et al.

[11] Patent Number: 6,004,327
[45] Date of Patent: *Dec. 21, 1999

[54] RATCHETING COMPRESSION DEVICE

[75] Inventors: Stanley Edwin Asnis; John Stephen Crombie, both of New York, N.Y.

[73] Assignee: Stryker Technologies Corporation, Kalamazoo, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/885,235

[22] Filed: Jun. 30, 1997

Related U.S. Application Data

[63] Continuation of application No. 08/706,383, Aug. 30, 1996, which is a continuation of application No. 08/550,549, Nov. 7, 1995, which is a continuation of application No. 08/101,601, Aug. 3, 1993.

[51] Int. Cl.$^6$ .................................................. A61B 17/00
[52] U.S. Cl. ............................................................ 606/104
[58] Field of Search .................................. 606/60–62, 65, 606/67, 72–73, 75, 105; 411/332, 372, 383–384, 388, 396

[56] References Cited

U.S. PATENT DOCUMENTS

| | | | |
|---|---|---|---|
| 1,373,045 | 3/1921 | Bernhard | 411/396 |
| 2,081,293 | 5/1937 | Davis . | |
| 2,143,922 | 1/1939 | Longfellow . | |
| 3,687,138 | 8/1972 | Jarvik . | |
| 3,842,824 | 10/1974 | Neufeld . | |
| 4,119,091 | 10/1978 | Partridge . | |
| 4,289,124 | 9/1981 | Zickel . | |
| 4,406,654 | 9/1983 | Bristow | 604/209 |
| 4,456,005 | 6/1984 | Lichty . | |
| 4,461,407 | 7/1984 | Finnegan . | |
| 4,655,199 | 4/1987 | Steffee | 606/61 |
| 4,688,561 | 8/1987 | Reese . | |
| 4,796,612 | 1/1989 | Reese . | |
| 4,903,692 | 2/1990 | Reese | 606/99 |
| 4,976,686 | 12/1990 | Ball et al. | 604/61 |
| 5,059,193 | 10/1991 | Kuslich | 606/62 |
| 5,167,664 | 12/1992 | Hodorek . | |
| 5,217,462 | 6/1993 | Asnis et al. | 606/73 |
| 5,250,049 | 10/1993 | Michael | 606/72 |
| 5,265,998 | 11/1993 | Kluser | 411/384 |
| 5,628,752 | 5/1997 | Asnis et al. | 606/104 |

FOREIGN PATENT DOCUMENTS

| | | | |
|---|---|---|---|
| 2289164 | 5/1976 | France | 606/61 |
| 95658 | 5/1939 | Switzerland | 606/66 |
| 475754 | 9/1969 | Switzerland . | |

*Primary Examiner*—Michael Buiz
*Assistant Examiner*—Vikki Trinh
*Attorney, Agent, or Firm*—Lerner, David, Littenberg, Krumholz & Mentlik, LLP

[57] ABSTRACT

A ratcheting compression device is provided which is very strong, which can be customized in length, which can be retightened periodically to maintain compression, which allows precise placement and alignment of bones with both grossly tuned compression and finely tuned compression, and in which only a limited inventory of parts is required. The two-piece compression device comprises (a) a novel first piece having a bone screw located at a first end thereof and having a ratcheting means located near the second end thereof and comprising teeth having their crests lying substantially in a plane and (b) a novel second piece comprising an anti-rotation means which acts in cooperation with the ratcheting means of the first piece to compress two segments of bone together.

In yet other embodiments, two embodiments of a driver are provided for quickly driving the stop onto the ratcheting means to a desired extent.

In a further embodiment, a customized method for compressing and fixing a first bone segment and a second bone segment together is provided.

5 Claims, 5 Drawing Sheets

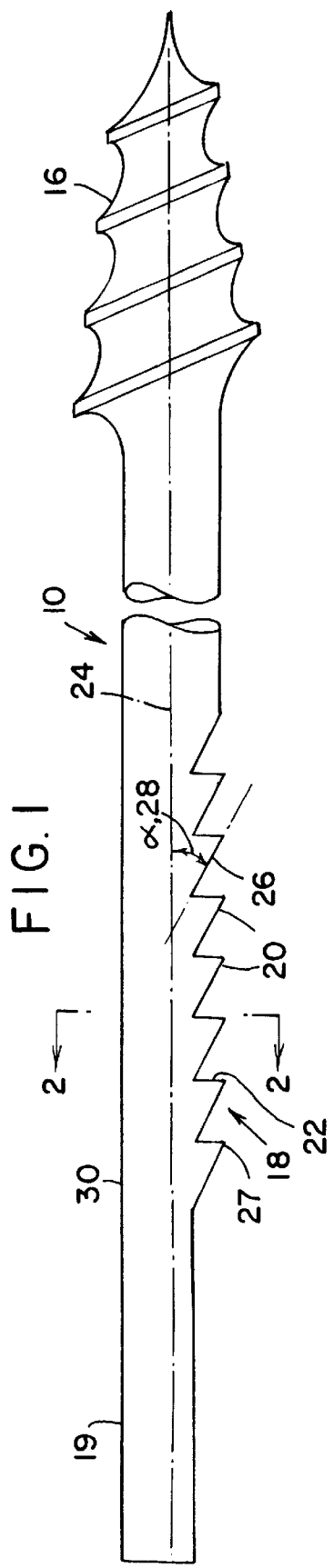
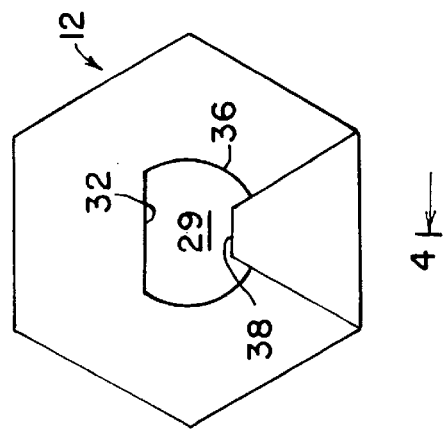
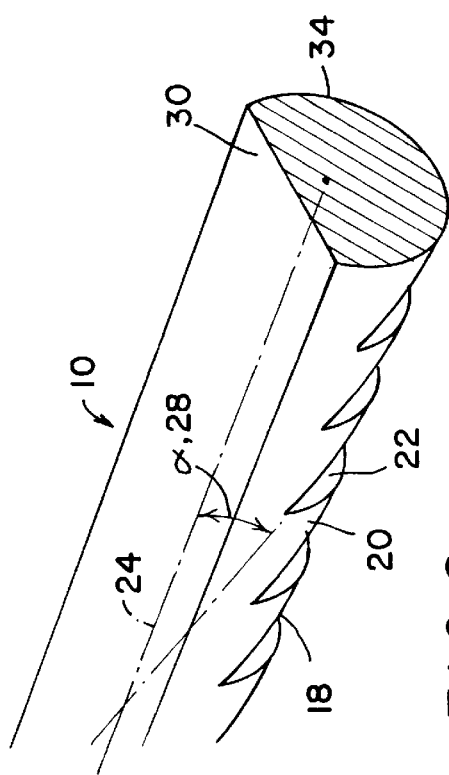

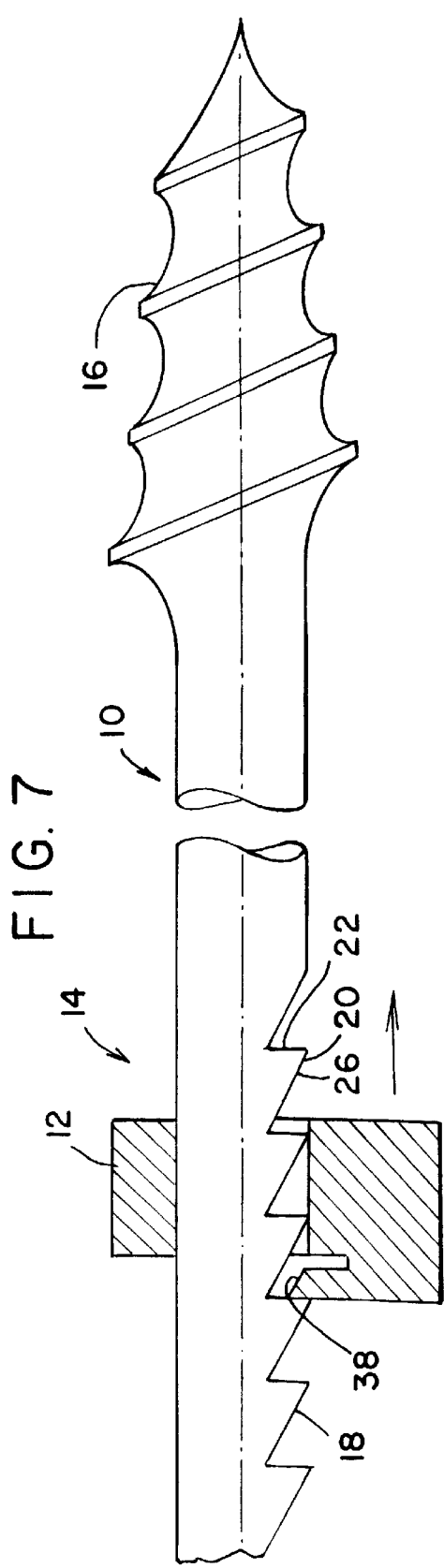
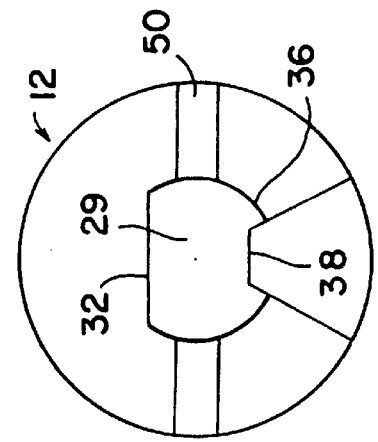
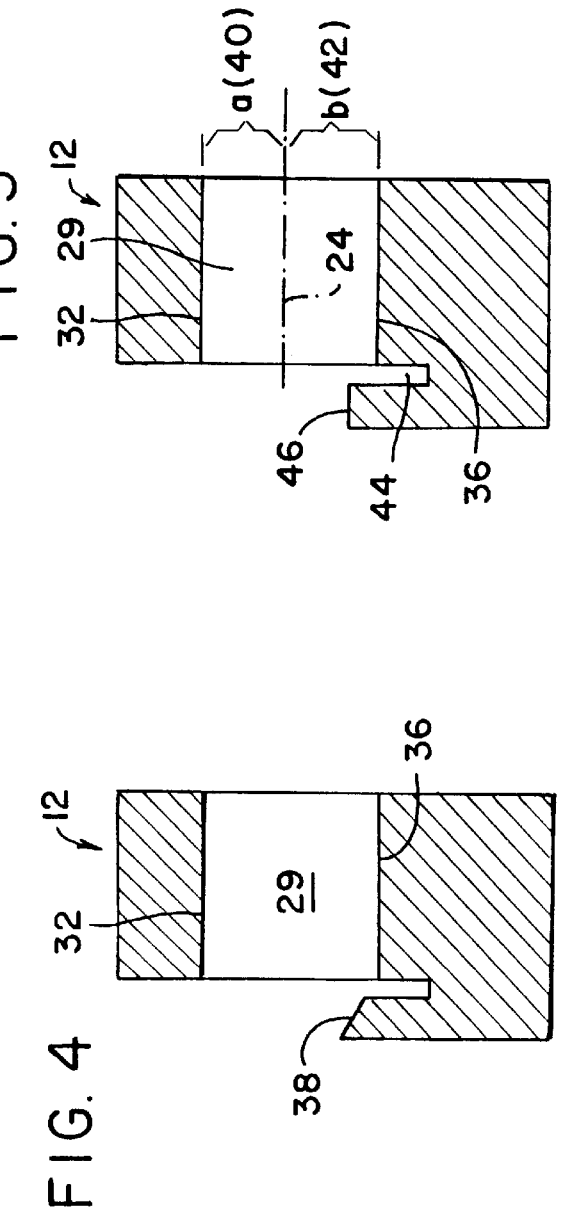
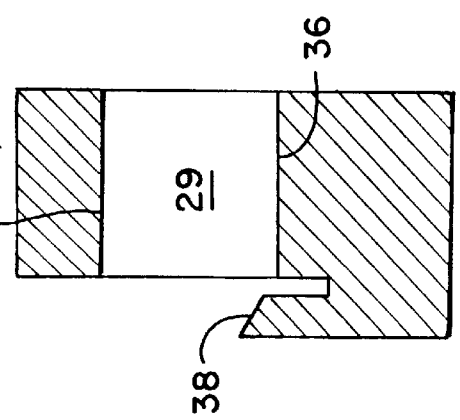

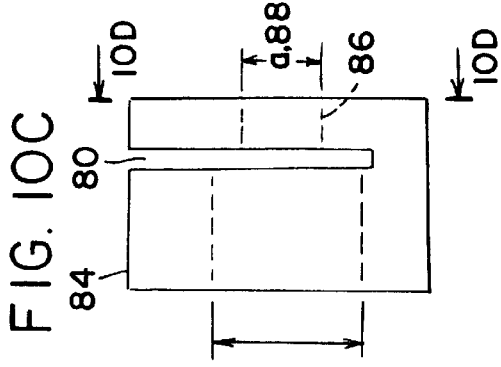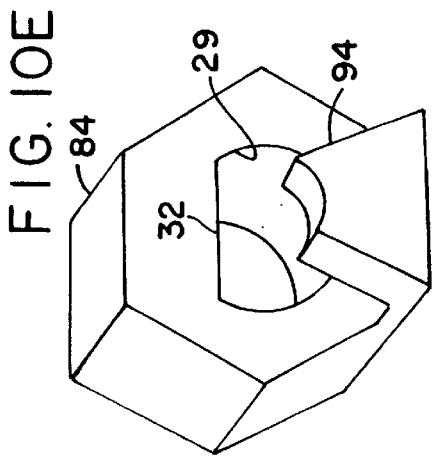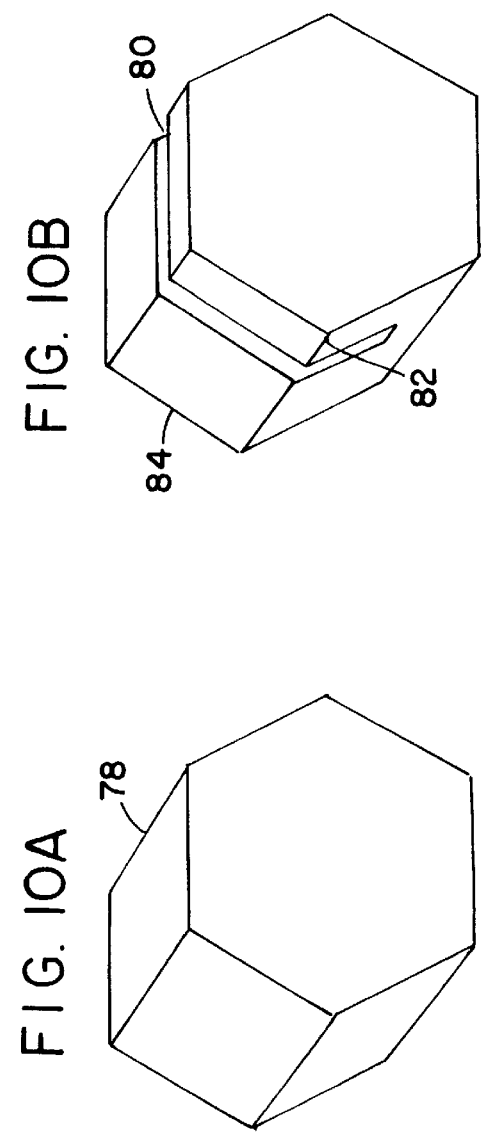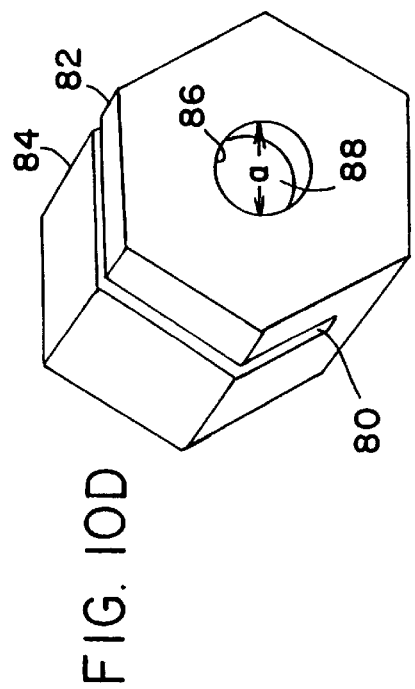

RATCHETING COMPRESSION DEVICE

This is a continuation of application Ser. No. 08/706,383 filed on Aug. 30, 1996, which is a continuation of application Ser. No. 08/550,549 filed on Nov. 7, 1995, which is a continuation of application Ser. No. 08/101,601, filed on Aug. 3, 1993.

FIELD OF THE INVENTION

This invention relates to orthopedic implants and relates in particular to orthopedic compression devices for compressing and clamping bone.

BACKGROUND OF THE INVENTION

In the prior art, a variety of devices for compressing bone have been known. See, for example, U.S. Pat. No. 4,456,005, U.S. Pat. No. 4,688,561, U.S. Pat. No. 4,796,612 and U.S. Pat. No. 5,217,462. In U.S. Pat. No. 5,167,664 a ratcheting bone screw is disclosed.

It is an object of this invention to provide another compression device which is very strong, which can be customized in length, which can be retightened periodically to maintain compression, which allows precise placement and alignment of bones with both grossly tuned compression and finely tuned compression, and in which only a limited inventory of parts is required.

SUMMARY OF THE INVENTION

These and other objects are satisfied by the ratcheting compression device of the invention.

According to the invention, a two-piece compression device comprises (a) a novel first piece having a bone screw located at a first end thereof and having a ratcheting means located near the second end thereof and comprising teeth having their crests lying substantially in a plane and (b) a novel second piece comprising an anti-rotation means which acts in cooperation with the ratcheting means of the first piece to compress two segments of bone together.

In a preferred embodiment, the novel anti-rotation means is a stop (e.g., nut or ball) with a keyed throughhole, the stop being specially formed to co-act with the ratcheting teeth so as to allow movement of the stop in only one direction and thereby to compress the segments of bone together and so as also to prevent rotation between the stop (or second piece) and the pin (or first piece).

In another preferred embodiment, the novel first piece according to the invention to be used with the special stop of the invention is a long cylindrical piece with a bone screw at one end and a ratchet component having ratchet teeth with their crests lying substantially in one plane (or a plurality of planes) at the other end.

In yet other embodiments, two embodiments of a driver of the invention are provided for quickly driving the stop onto the ratcheting means to a desired extent.

In a further embodiment, a customized method for compressing and fixing a first bone segment and a second bone segment together comprises:

(a) drilling the first end of the elongated piece of the device of the invention through the first bone segment and into the second bone segment (or inserting the elongated piece into a pre-drilled hole) and advancing the screw threading of the device of the invention as far as desired;

(b) ratcheting the second piece of the device of the invention down onto the ratchet component of the first piece of the device of the invention as far as desired so as to provide a gross compression adjustment to nearly the final compression adjustment; and (c) turning the first piece or the second piece of the device of the invention (and thus also the second piece or the first piece, respectively, neither part being able to rotate with respect to the other piece) so as to provide fine compression adjustment.

Also according to the invention, step (b) is preferably done quickly with the ratcheting gun of the invention.

Also according to the invention, an optional additional step of cutting off the elongated piece to a desired extent is preferably done, either following or immediately preceding step (c), after gross compression adjustment has been done.

DESCRIPTION OF THE PREFERRED EMBODIMENTS

BRIEF DESCRIPTION OF THE DRAWINGS

FIG. 1 is a plan view of an embodiment of the first piece of the invention of the compression device of the invention, showing the ratcheting means at one end thereof and the bone screw at the other end thereof.

FIG. 2 is an elevational view, partially in cross-section of the ratcheting means of FIG. 1, as taken along the line 2—2 in FIG. 1.

FIG. 3 is a plan view of an embodiment of the second piece of the compression device of the invention, which acts in cooperation with the first piece of the device as shown in FIG. 1, with an anti-rotation means (in the form of a keyed stop) which acts with the ratcheting means shown in FIG. 1 so as to compress two segments of bone together, this keyed stop being (in one embodiment) a hex nut.

FIG. 4 is a cross-sectional view of the hex nut shown in FIG. 3 as taken along the line 4—4 in FIG. 3.

FIGS. 5 and 6 are alternative embodiments of a keyed stop (e.g., hex-nut or ball) of the device of the invention.

FIG. 7 is a plan view, partially in cross section of an embodiment of an assembled two-piece device of the invention, showing the embodiments of FIG. 1 and of FIG. 4 assembled together in combination.

FIG. 10 is an illustration of steps used to produce an embodiment of a keyed stop of the invention.

DETAILED DESCRIPTION OF THE DRAWINGS

Figure 8:
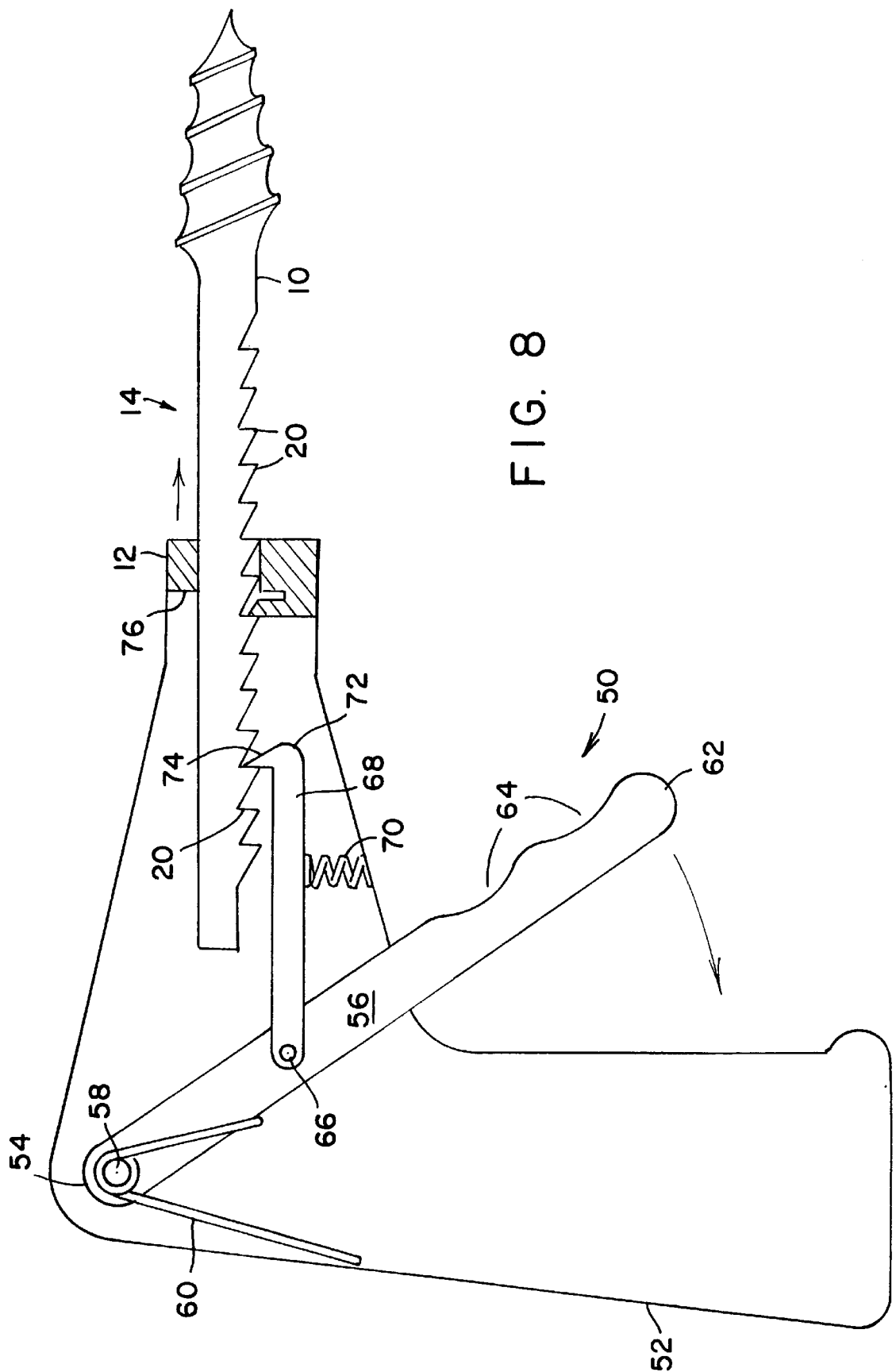
FIGS. 8 and 9 show schematic illustrations of alternative embodiments of a driver of the invention for use in driving the keyed nut down onto the ratcheting means of the first piece of the device of the invention.

Referring to the drawing, shown in FIG. 1 is an embodiment of a first piece 10 of the invention to be used in combination with an embodiment of a second piece 12 of the invention (shown in FIGS. 3 through 6), so as to provide an embodiment of the compression device of the invention 14 (shown assembled together in FIG. 7). First piece 10 is a pin having located at (or near) its distal end a bone thread 16 and having located near its mid-portion ratcheting means 18 and having preferably a substantially smooth portion 19 at or near its proximal end. Ratcheting means 18 comprises preferably asymmetric teeth 20 which are located preferably on only one surface of first piece 10 and are located at the proximal end thereof. Asymmetric teeth 20 are angled as shown in FIG. 1 and in FIG. 7, with one side 22 of each tooth being substantially perpendicular to the centerline 24 of first piece 10, and with the other side 26 of each tooth (when extended) forming an angle α 28 with centerline 24. Angle α 28 is an acute angle. The crests 27 of the teeth 20 lie in a single plane in this embodiment (or alternatively in another embodiment the teeth can lie with their crests in a plurality of planes).

In FIG. 2, ratcheting means 18 is shown partially in cross-section, taken along the line 2—2 in FIG. 1, with centerline 24 and angle α 28 shown. As clearly shown in FIGS. 1 and 2, first piece 10 can be formed from a pin (e.g., an Apex® pin sold by Howmedica) having a bone thread 16 at one end thereof and a smooth portion 19 at the other end thereof and by machining the mid-portion of the pin to provide a flat surface 30 on the pin and by machining opposite to that flat surface the asymmetric teeth 20 which were described above.

In FIG. 3, an embodiment of second piece 12 is shown in the form of a hex nut which has been machined so that it has a keyed throughhole 29 with a flat surface 32 which corresponds substantially to the flat surface 30 on first piece 10 and with a curved portion 36 which corresponds substantially to the curved portion 34 on first piece 10. Second piece 12 as shown in FIG. 3 also has a flexible interference lip 38 (which is preferably an integral part of second piece 12) for mating with the asymmetric teeth 20 (described below and shown assembled together in FIG. 7).

In FIG. 4, second piece 12 is shown in cross-section, with flexible interference lip 38, which interacts in combination with asymmetric teeth 20, as described below.

In FIG. 5, second piece 12 is shown in cross-section. A keyed throughhole 29 is broached to produce a flat surface 32 and a curved portion 36 positioned at a distance a (40) and b (42), respectively, from the centerline 24.

The production is described further below with reference to FIG. 10.

Integral portion 46 is preferably cut so that it has the shape of interference lip 38 which will coact with asymmetric teeth 20. (Thus, inference lip 38 will have preferably substantially the shape of an asymmetric tooth which can fit within the space between any two adjacent asymmetric teeth 20.)

In FIG. 6, an alternative embodiment of second piece 12 is shown, in the form of a ball or cylinder, having a keyed throughhole 29, with a flat surface 32 and a curved portion 36. Additionally, flexible interference lip 38 is present. Also slot 50 is shown. Slot 50 is used for rotating the stop 12 (as a receptacle for the driver).

In FIG. 7, first piece 10 of the invention and second piece 12 of the invention are shown assembled together so as to provide the ratcheting compression device 14 of the invention. Second piece 12 has been positioned quickly onto first piece 10 by a driver (described below with reference to FIG. 8), second piece 12 being movable in only one direction (as shown by the arrows in FIG. 7). Flexible interference lip 38 is shown in mating position within ratcheting means 18, which is preferably asymmetric teeth 20.

Figure 9:
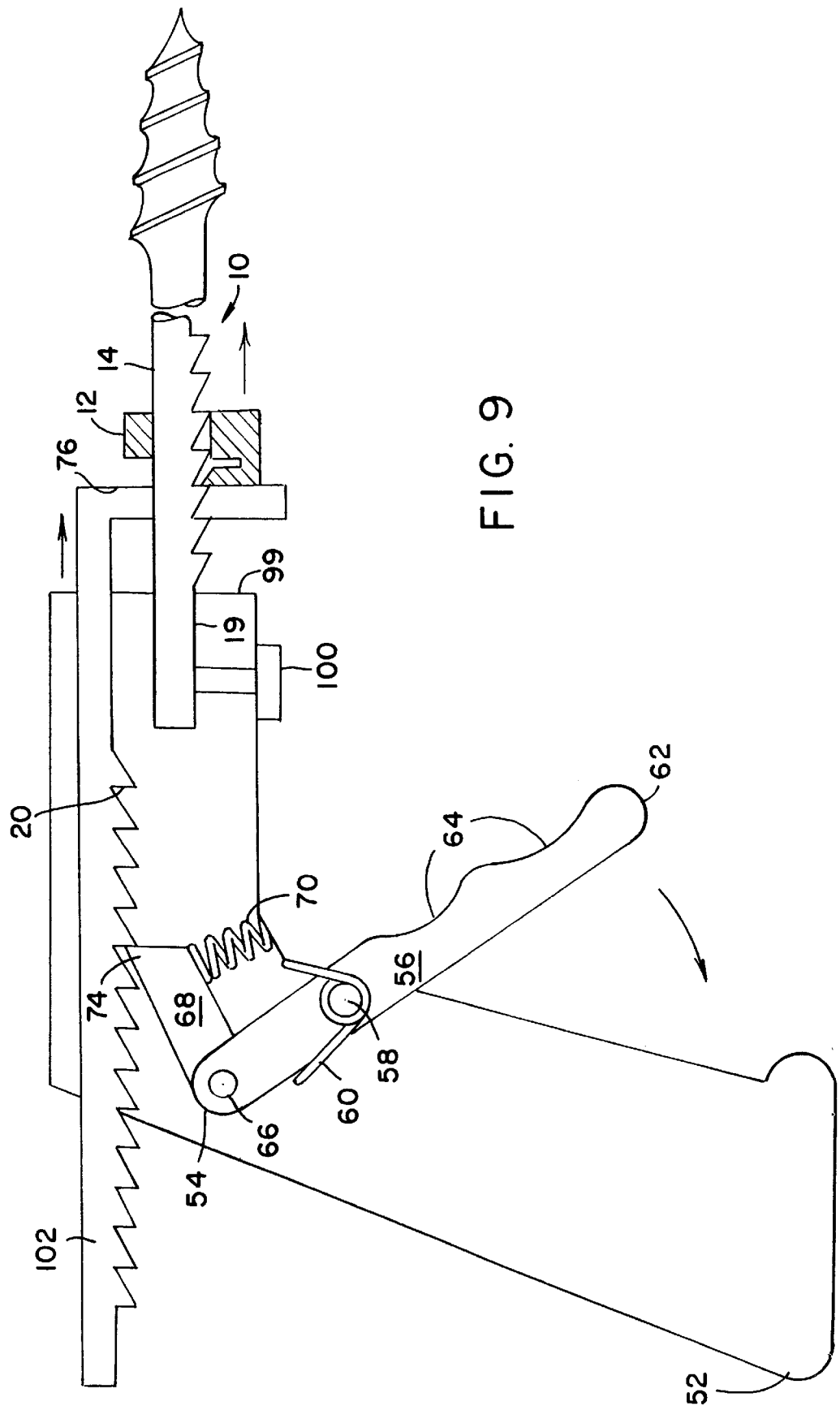

In FIGS. 8 and 9, schematic illustrations of alternative embodiments of a driver suitable for assembling second piece 12 onto first piece 10 are shown.

In FIG. 8, a specially-designed ratcheting gun 50 for use in inserting the compression device 14 of the invention is shown in cross-section. The ratcheting gun 50 has a main body portion 52, which houses therewithin a first end 54 of trigger 56. First end 54 is attached to main body portion 52 by a pivot pin 58 and is maintained in its position in a relaxed state by a torsion spring 60. The second end 62 of trigger 56 extends outside main body portion 52 and has indentations 64 for enabling trigger 56 to be easily grasped. Trigger 56 also has attached thereto at pivot 66 a prong 68 which is supported by spring 70 within main body portion 52. Prong 68 has a second end 72 which has a cooperating portion 74 which fits within each (one at a time) of the asymmetric teeth 20 of the compression device 14 of the invention when spring 70 is in its relaxed position.

In the operation of ratcheting gun 50 in FIG. 8, trigger 56 is pulled back towards main body portion 52 and against the action of torsion spring 60, thereby causing cooperating portion 74 of second end 72 to be pulled against one of the asymmetric teeth 20 (as shown in FIG. 8 towards the left). Second piece 12 which is positioned adjacent to interacting end 76 of ratcheting gun 50 is forced thereby to the right as depicted by the arrow in FIG. 8) and the entire gun 50 moves so as to move second piece 12. Interacting end 76 (corresponding to a muzzle end) of ratcheting gun 50 is specially shaped so that it cooperates with second piece 12.

To assemble this embodiment of the device of the invention one can use the gun as a holder for the stop 12. Then one can manually insert first piece 10 through the stop (or second piece) 12. When ratcheting means 18 engages with second end 72 of prong 68, one then positions the stop 12 on the interacting end 76 of the gun 50 and then manually inserts first piece 10 through the stop (or second piece) 12 into the gun 50. When the first of the asymmetric teeth 20 engages with the second end 72 of prong 68, one can use the trigger 56 to continue the compression mechanically.

In FIG. 9, an alternative embodiment of a ratcheting gun is shown in cross-section. Corresponding parts are numbered as in FIG. 8. This embodiment of the gun has an independent ratcheting pusher rod 102 (independent of the ratchet teeth of the pin 10) and has a holder 100 (which can be a pin lock, for example). In this embodiment, the pusher rod 102 (having interacting end 76 as integral part thereof) moves so as to move second piece 12. The gun 50 provides the mechanical advantage to get the second piece 12 engaged with the first of the asymmetric teeth 20.

In FIG. 10, the steps in the manufacture of second piece 12 are depicted schematically, in FIGS. 10a through 10e. In FIG. 10a, a hex-shaped piece of metal 78 is shown. In FIG. 10b, that same piece of metal 78 is shown after a slit 80 has been cut into the hex-shaped piece 78, but only partially therethrough. In FIG. 10c, slit 80 is positioned such that it forms a first, smaller portion in the hex-shaped piece of metal 78 and a second, larger portion 84. As shown in FIG. 10c, first smaller portion 82 is then drilled so as to produce a hole 86 having a diameter a 88; and second (larger) portion 84 is broached (or otherwise shaped) so as to produce a keyed throughhole 29 (which is D-shaped, for example).

FIG. 10d is taken along the line X–X' in FIG. 10c with corresponding parts labeled correspondingly. In FIG. 10e, in the final step of the production of the ratcheting screw (or second piece 12), the major portion of first (smaller) portion 82 in hex-shaped piece of metal 78 is removed, leaving behind tab 94. If desired, tab 94 can be shaped so that it appears as in FIG. 5 with a flat 46; or alternatively, if desired, it can be shaped so that it is angled as shown in FIG. 4 at flexible interference lip 38.

The specially shaped stop of the invention is preferably machined from one piece of metal (which can be any material that is suitable for implants, for example stainless steel). The stop has an outer flange which can be in the shape of a hexagon or round or any other suitable shape, as desired. The stop preferably has a keyed throughhole with a flexible interference lip.

The pin of the invention has at or near its distal end any suitable bone thread. It has asymmetric teeth which are preferably located on one surface near the mid-portion of the pin. Alternatively, teeth can be provided on more than one flat surface, as desired, for example on two or three or more surfaces. The pin also preferably has a smooth portion at the proximal end thereof, although it is not absolutely required.

The two-piece implant of the invention provides precise placement and alignment of bones (using the shaft or pin portion), and the specially designed stop (or nut) portion of the device provides (together with the first portion or pin portion or shaft portion) compression and fixation of bones. The shaft or pin portion is cut off to provide a customized device length or left on to provide a custom length screw with a long driving shaft.

The two piece device of the invention is inserted in the following manner. The pin is first driven into and through a first bone segment and then into a second bone segment in the same manner as a threaded pin is driven into bone. Next, the stop of the invention is ratcheted down onto the ratchet component, preferably with the ratchet gun of the invention, as far as desired and nearly to the position of the final compression adjustment, thus providing a gross compression adjustment. The teeth of the ratchet are angled such that the stop can be driven down only in one direction. The shape of the throughhole in the nut and the shape of the pin (i.e., the shape of the first piece 10 and second piece 12) mate in such a way that the nut cannot rotate on the pin. If the first compression described above has resulted in the screw tip advancing more than desired, the combination of the screw and bone pin can be backed out by turning the combination of the two part device as a screw; and, if desired, the screw can then be further shortened with the ratchet. Alternatively, if desired, the combined device can be advanced further, by turning the combined device as a screw and performing the final compression as a lag screw. After the compression has been completed, the end of the device opposite the threading can, if desired, be left so that it protrudes out of the skin or alternatively, it can be cut off, if desired, so as to provide a customized device length.

The two-piece device of the invention has significant advantages over other known devices. Due to the capabilities of length customization described above, only a limited inventory of parts is required. The device is very versatile, and with only a few types of threaded pins and with a few different shapes of nuts, many combinations can be made. One can customize the screw length by cutting off the ratcheting portion, as desired. One can achieve gross compression very rapidly by use of the ratchet and one can then follow that compression by a very fine adjustment of compression by use of the device as a lag screw and by rotating the two-part device. The bone thread also can be initially placed into the bone very quickly with a drill to almost its final length, and the compression can be achieved very quickly with the ratchet. The final compression with the lag screw can be made, and if the screw tip has advanced too much, the device can be backed out and can be shortened in length with the ratchet so as to provide additional compression. The device provides options of either having the end opposite the bone thread be left protruding out of the skin or cut off; if it is left protruding out of the skin, the compression can be adjusted (either increased or decreased) or the entire device can later be removed without further surgery. This option provides both an external and internal fixation device. The device provides a very strong compression device, and even devices of very small sizes will be very strong due to the design of the device, which features a solid core of metal through the entire pin. The pin portion can be used through jigs to aim the device under fluoroscopy; this is not possible with a classical screw where the screw head interferes with the jig.

Further advantages of the compression device 14 of the invention are that the device can be driven by turning either first piece 10 or second piece 12, and it is not necessary to remove the shaft (or first piece 10) to perform this compression.

The pin can be self-drilling and can be used with any combination of jigs.

In performing surgery, the surgeon is not always sure what length of the pin is needed to produce the desired compression. However, with the device of this invention, the length can be adjusted (as described herein).

Because the tab is made of metal, the device of the invention is very strong and rigid and the ratcheting gun 50 as described herein is generally needed to insert the second piece 12. Because of the asymmetric teeth 20 of the first piece 10, the second piece 12 can be moved only in one direction and cannot be removed from the first piece 10, thus providing a compression device 14. The device of the invention 14 can be removed as a one piece device (as a normal screw would be removed) by rotating the stop 10.

We claim:

1. An implant for compressing a first bone segment and a second bone segment together, said implant comprising:
    (a) an antirotation element having a D-shaped bore; and
    (b) a first elongated piece in the shape of a rod and having a first end and a second end and having a solid inner core throughout said entire first elongated piece and having a D-Shaped cross-section along a portion of said first piece between said first and second ends to be used in cooperation with said antirotation element and comprising:
        (1) a screw threading located at least substantially adjacent to said first end and
        (2) a ratchet portion having a D-Shaped cross-section extending from adjacent said screw thread toward said second end and having a smooth, flat longitudinal surface forming the flat surface of said substantially D-shaped cross-section and further comprising teeth extending across a curved surface of said D-shaped portion which are positioned near said second end and having their crests lying substantially in a plane.

2. An implant for compressing a first bone segment and a second bone segment together, said implant comprising:
    (a) an elongated piece having a bone screw portion adjacent one end and a D-shaped ratchet portion adjacent said bone screw portion extending towards said second end and
    (b) an antirotation element having a D-shaped bore for use in cooperation with said elongated piece, wherein said antirotation element is to be ratcheted down along said ratchet portion having a smooth, flat longitudinal surface forming the flat portion of said substantially D-shaped ratchet portion, located on said elongated piece so as to compress said first bone segment and said second bone segment together and wherein said stop has a lock component comprising a flexible interference lip which locks with teeth of said ratchet portion in a manner such that said stop can be moved only in one direction with respect to said ratchet portion of said elongated piece said stop is locked rotationally with respect to said elongated piece by the engagement of said D-shaped bore and said D-shaped ratchet portion.

3. An implant according to claim 2, wherein said first elongated piece has a solid inner core, a centerline I and a flat surface, and wherein teeth sand of said ratchet portion are positioned substantially opposite to said flat surface.

4. An implant for compressing together two segments of a bone, said implant comprising a pin having:

a longitudinal pin axis and a first end and a second end;

a bone thread located at said first end of said pin;

a smooth segment located at said second end of said pin; and a ratchet segment having a portion with a substantially D-shaped cross-segment and having a smooth, flat longitudinal surface forming the flat of said D-shaped cross-segment and a rounded surface forming a curved part of said D-shaped cross-segment said portion located between said bone thread at said first end and said second end and starting adjacent said bone thread and said portion having notched teeth notched into said curved of part of said D-shaped cross-section, with each of said notched teeth having a first surface which is cut perpendicular to said flat surface and a second surface which is cut at an acute angle with respect to said flat surface, wherein said first surface and said second surface meet at a meeting line, and wherein said meeting line of each of said notched teeth lies in a plane P which is parallel to said flat surface of said D-shaped cross-section.

5. The implant of claim 4 further comprising an antirotation member sized and configured to cooperate with the ratchet segment, the antirotation member having a lock component which locks with teeth of the ratchet segment so that the antirotation member can be moved only in one direction and is rotationally locked with respect to the ratchet segment.

* * * * *

UNITED STATES PATENT AND TRADEMARK OFFICE
CERTIFICATE OF CORRECTION

PATENT NO. : 6,004,327
DATED : December 21, 1999
INVENTOR(S) : Asnis et al.

It is certified that error appears in the above-identified patent and that said Letters Patent is hereby corrected as shown below:

Column 7, line 1, cancel the word "first".
Column 7, line 3, before "teeth" insert -- said -- and cancel the word "sand".
Column 8, line 2, cancel the word "of" (first occurrence).

Signed and Sealed this

Twenty-third Day of January, 2001

Attest:

Q. TODD DICKINSON

Attesting Officer

Commissioner of Patents and Trademarks